(12) United States Patent
King et al.

(10) Patent No.: US 10,535,821 B2
(45) Date of Patent: Jan. 14, 2020

(54) SMALL MOLECULE ACCEPTORS DERIVED FROM RENEWABLE FURAN SOURCE

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 126 days.

(21) Appl. No.: 15/377,828

(22) Filed: Dec. 13, 2016

(65) Prior Publication Data
US 2018/0166631 A1    Jun. 14, 2018

(51) Int. Cl.
*H01L 51/00* (2006.01)
*C07D 493/04* (2006.01)
*C08G 61/12* (2006.01)

(52) U.S. Cl.
CPC ........ *H01L 51/0036* (2013.01); *C07D 493/04* (2013.01); *C08G 61/126* (2013.01); *C08G 2261/124* (2013.01); *C08G 2261/228* (2013.01); *C08G 2261/3223* (2013.01); *C08G 2261/3243* (2013.01); *C08G 2261/3246* (2013.01); *C08G 2261/411* (2013.01); *C08G 2261/91* (2013.01); *H01L 51/0043* (2013.01)

(58) Field of Classification Search
CPC . H01L 51/0036; C07D 493/04; C08G 61/126; C08G 2261/124; C08G 2261/228; C08G 2261/3223; C08G 2261/3242; C08G 2261/3243; C08G 61/125
See application file for complete search history.

(56) References Cited

U.S. PATENT DOCUMENTS

| | | |
|---|---|---|
| 8,269,099 B2 | 9/2012 | Kitazawa et al. |
| RE44,304 E | 6/2013 | Marks et al. |
| 8,552,179 B2 | 10/2013 | Lazarev |
| 8,946,697 B1 | 2/2015 | Ma et al. |
| 9,163,174 B2 | 10/2015 | Alleyne et al. |
| 9,184,399 B2 | 11/2015 | Dyatkin et al. |
| 9,190,621 B2 | 11/2015 | Ma et al. |
| 9,190,623 B2 | 11/2015 | Kwong et al. |
| 2012/0008068 A1* | 1/2012 | Doi ........................ C08G 61/02 349/69 |
| 2014/0167002 A1 | 6/2014 | Welch et al. |
| 2015/0249214 A1 | 9/2015 | Watanabe et al. |

FOREIGN PATENT DOCUMENTS

| | | | |
|---|---|---|---|
| KR | 20160024250 A | * | 3/2016 |
| WO | 2016/062258 A1 | | 4/2016 |

OTHER PUBLICATIONS

Stenzel-Rosenbaum, Martina H., et al. "Synthesis of poly (styrene) star polymers grown from sucrose, glucose, and cyclodextrin cores via living radical polymerization mediated by a half-metallocene iron carbonyl complex." Macromolecules 34.16 (2001): 5433-5438. (Year: 2001).*

* cited by examiner

*Primary Examiner* — Nicholas E Hill
(74) *Attorney, Agent, or Firm* — Patterson + Sheridan, LLP

(57) ABSTRACT

Embodiments described herein provide a precursor for synthesizing a number of molecules for use in organic photovoltaics. The precursor is diiodo-furopyran (DFP), such as dibromo-DFP (DBDFP), to be used to synthesize a number of different molecules for use in organic photovoltaics. DFP possesses numerous reactive sites that can be used to simultaneously modify the backbone structure (which can be used to tune electronic and crystalline properties) and the side-chains (affecting the solubility and the solubility of any subsequent copolymers). Each of the molecules has either a biisocoumarin or biisoquinoline core structure and can be easily varied to yield a different functional backbone or different substituents. The molecules can be used in copolymers or small molecules for use in OPVs.

14 Claims, 6 Drawing Sheets

A: HNR$_2$, Pd(dba)$_2$, P(o-Tol)$_3$, NaO$t$Bu
B: [Cu], AgF
C: i) Pd(PPh$_3$)$_2$Cl$_2$, NEt$_3$, ≡—R   ii) H$_2$, Pd/C
D: NH$_4$OH, heat
E: H$_2$NR, heat
F: fac-Ir(ppy), HCO$_2$H, $^n$Bu$_3$N, flow reactor, ii) H$_2$NR, heat
G: HNR$_2$, Pd(dba)$_2$, P(o-Tol)$_3$, NaO$t$Bu
H: H$_2$NR, heat

SMALL MOLECULE ACCEPTORS DERIVED FROM RENEWABLE FURAN SOURCE

BACKGROUND

The present disclosure relates to organic photovoltaic monomers, oligomers, and polymers, and more specifically, to methods of synthesizing a number of molecules for use in organic photovoltaics.

Organic electronics have drawn research interest in recent years because of the potential for broad commercial application, including electroluminescence devices, field effect transistors, and organic photovoltaic ("OPV") devices, among other uses. In all these devices, the key component is organic semiconducting material, which is usually used as one or more active thin layers. OPVs offer a practical path to achieve low-cost, renewable energy. OPVs have several advantages that inorganic counterparts lack that allows for strong potential of lower cost implementation. The advantages of OPVs include the ability to be solution processed into large-area thin-films, to be fabricated into lightweight and flexible devices, and the capacity to tune their properties through organic synthesis.

One problem common to organic solar cells is in achieving polymers and small molecules that are soluble enough in common organic solvents rendering them solution processable, while still maintaining a high degree of crystallinity, which allows for optimal charge separation and transport. This problem is usually dealt with by affixing alkyl side chains to the aromatic molecules that make up the polymer (or small molecule) backbone. The vast majority of polymers that have been successfully used in OPVs include an alternating electron-rich (donor) and electron-deficient (acceptor) comonomers, called donor-acceptor (D-A) copolymers. Typically, it is much easier, for synthetic reasons, to affix alkyl chains to the donor molecules. For this reason, the library of known, alkyl chain-functionalized donor molecules is much more diverse than that of the acceptor molecules. There exists a need for a modifiable acceptor scaffold that can also be easily modified with various alkyl side-chains for improved solubility.

SUMMARY

In one embodiment, a precursor for forming a polymer or small molecule to be used in organic photovoltaics includes a compound having the structure:

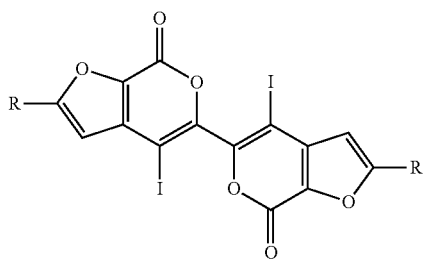

wherein R is bromine, hydrogen, chlorine or trifluoromethanesulfonate.

In another embodiment, a method includes dimerizing a functionalized furan dimethyester (FDME) to form a FDME dimer, performing a reaction at one ester group of each functionalized FDME of the FDME dimer to form a pyranone structure fused to each furan group of the FDME dimer to yield a diiodofuropyranone structure, and replacing the remaining ester groups of the diiodofuropyranone structure to form a 2-substituted iodofuropyranone dimer.

In another embodiment, a method for forming a polymer or small molecule to be used in organic photovoltaics includes forming a molecule using dibromo-diiodo-furopyran.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
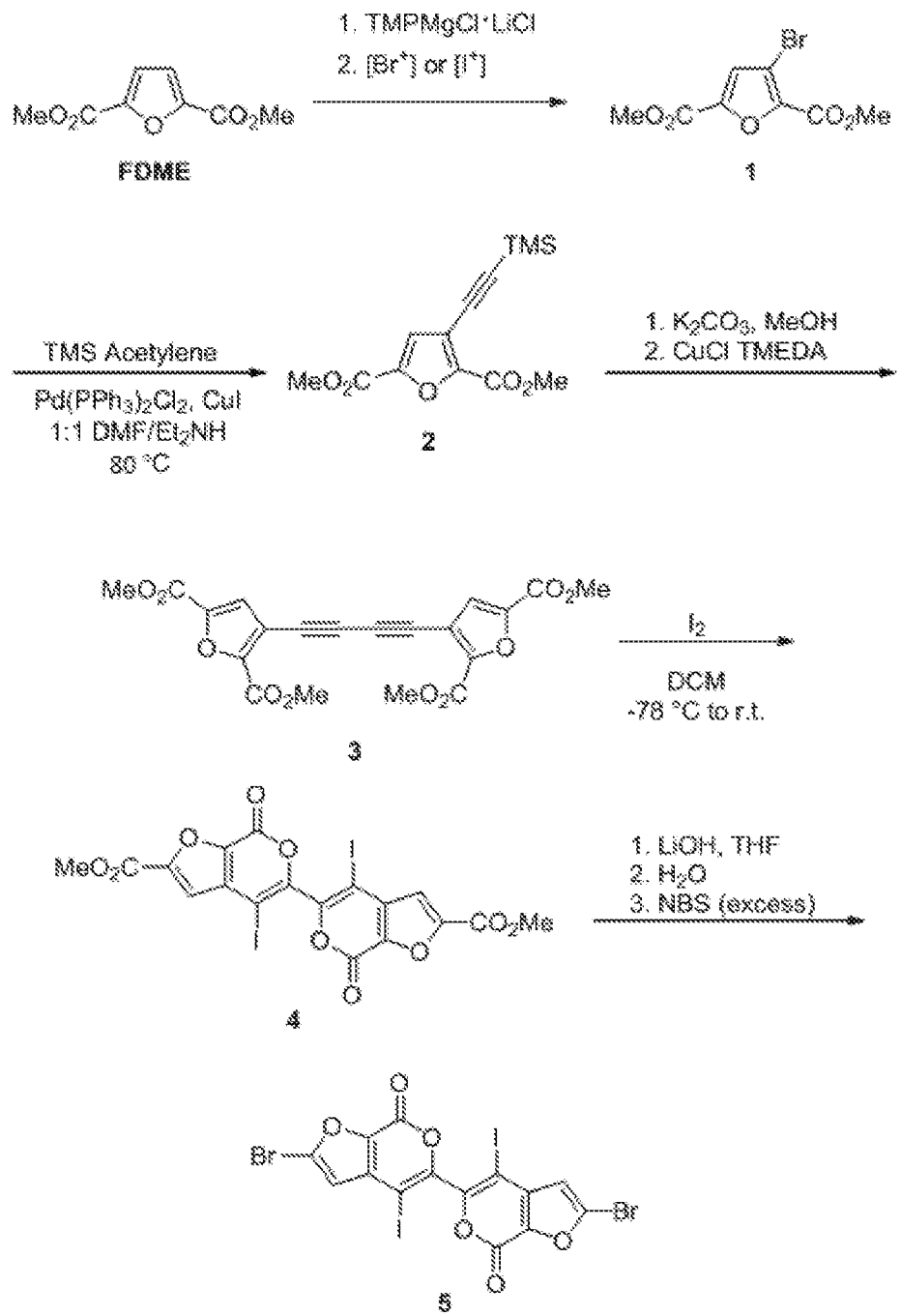
FIG. 1 is a chemical reaction diagram illustrating a method of forming a dibromo-diiodo-bifuropyranone heterocycle according to at least one embodiment.

Embodiments described herein provide a precursor for synthesizing a number of molecules for use in OPV devices. The precursor has a diiodo-furopyran ("DFP") structure, such as dibromo-DFP ("DBDFP"), which can be used to synthesize a number of molecules useful as reactants in forming OPV polymers. DFP possesses numerous reactive sites that can be used to simultaneously modify the backbone structure (which can be used to tune electronic and crystalline properties) and the side-chains (affecting the solubility and the solubility of any subsequent copolymers). Each of the molecules has either a biisocoumarin or biisoquinoline core structure and can be easily varied to yield a different functional backbone or different substituents. The molecules can be used in OPV copolymers or small molecules for use in OPVs.

As described herein, the terms "substituent", "radical", "group", "moiety" and "fragment" may be used interchangeably to indicate a point of attachment to a molecule.

As described herein, "alkyl" embraces a linear or branched acyclic alkyl radical containing from 1 to about 16 carbon atoms. In some embodiments, alkyl is a $C_{1-10}$ alkyl, $C_{1-7}$ alkyl or $C_{1-5}$ alkyl radical. Examples of alkyl include methyl, ethyl, propyl, isopropyl, butyl, isobutyl, tert-butyl, sec-butyl, and pentan-3-yl.

Chemical structures are presented herein using the following general notation:

[structure]$_n$

This notation is intended to define a repeated chemical structure within a larger structure, or molecule. Use of brackets around a chemical structure, with a letter subscript "n" generally indicates that the structure is repeated "n" times. Letters other than "n" may be used, and in each case, the letter subscript stands for a positive integer of at least 3. Unless otherwise noted, there is no theoretical upper limit to the value of the subscript. The notation is intended to refer to all possible polymers, of any feasible size, having the structure. However, kinetic and thermodynamic circumstances of individual chemical reactions, such as viscosity, temperature, and monomer availability may limit the growth of polymers in specific cases.

The chemical structures in this disclosure may denote atomic composition of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals surfaces, isoelectronic surfaces, and the like may vary among instances of the same chemical compound. Additionally, unless otherwise noted, the disclosed structures cover all enantiomers, diastereomers, cis/trans isomers, conformers, rotamers, and topomers of the represented compounds. All reactions described herein are performed at nominal conditions (i.e. room temperature to 50° C.) unless otherwise specified.

Recently, a new low-cost method has been reported to produce furan dimethyester (FDME) from renewable sources. DFPs such as DBDFP can be synthesized using FDME as a renewable building block. DBDFP can be synthesized as shown in FIG. 1.

In FIG. 1, bio-renewable FDME is converted into 3-bromo-FDME (1) by reacting FDME with 2,2,6,6-tetramethylpiperidinylmagnesium chloride-lithium chloride complex (TMPMgCl·LiCl), which is a commercially available reagent, followed by quenching with an electrophilic bromine or iodine source. Electrophilic bromine sources include elemental bromine, N-bromosuccinimide ("NBS"), and benzenesulfonyl bromide. Electrophilic iodine sources include elemental iodine, N-iodosuccinimide, and 1,2-diiodoethane. A Sonogashira cross-coupling reaction is then performed using trimethylsilyl (TMS) acetylene to give the protected alkylnyl-FDME (2). A deprotection of the TMS group, followed by a Glaser-Hay homocoupling of (2), results in a 1,3-bisalkyne (3). Reaction of bisalkyne (3) with iodine (or iodine monochloride in some cases) results in diiodo-dimethyl ester-bifuropyranone heterocycle (4) (IUPAC name of a single heterocycle: 7H,7'H-[5,5'-bifuro[2,3-c]pyran]-7,7'-dione). This step is performed under cryogenic conditions of −78° C. at first, and the mixture is allowed to warm to room temperature naturally as the reaction proceeds. The methyl ester groups are then converted into carboxylic acid groups via saponification, which are then replaced with bromine atoms in a one-pot procedure, giving DBDFP (dibromo-diiodo-bifuropyranone) heterocycle (5). FIG. 1 is a "one-pot" synthesis performed in a suitable solvent, for example an organic solvent such as toluene or dimethylformamide (DMF), where at each step the reagents for performing that step are added to the mixture to achieve the incremental result.

Figure 2:
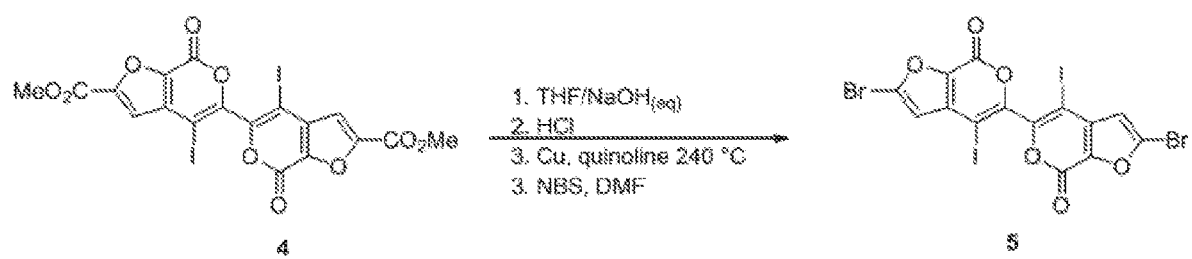
FIG. 2 is a chemical reaction diagram illustrating a method of forming a dibromo-diiodo-bifuropyranone heterocycle according to at least one embodiment.

Instead of the one-pot procedure of replacing the methyl ester groups with bromine atoms as shown in FIG. 1, FIG. 2 shows multi-step replacement of methyl ester groups with bromine atoms. As shown, the first step is saponification of the diiodo-dimethyl ester-bifuropyranone heterocycle (4) by NaOH (or alternatively MgCl$_2$/KI) in THF. Then the product of the first step is acidified by HCl in the second step. At the third step, a copper powder-catalyzed decarboxylation in quinoline is performed on the product of the second step, followed by bromination using NBS as a reagent and DMF as a solvent.

In some embodiments, the bromine atoms in compound (5) may be replaced with protons (hydrogen atoms), chlorine atoms, or trifluoromethanesulfonate (OTf) groups. Thus, the precursor has a structure:

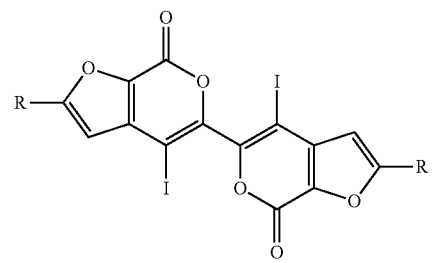

where R is Br, H, Cl, or OTf.

The DBDFP heterocycle (5) can be used as a precursor, or a molecular scaffold, to synthesize various molecules based on different reaction conditions. The molecules synthesized using the precursor can be used in OPV copolymers or small molecules for use in OPVs. The various molecules synthesized using the DBDFP heterocycle (5) and the corresponding reaction conditions are shown in FIG. 3.

Figure 3:
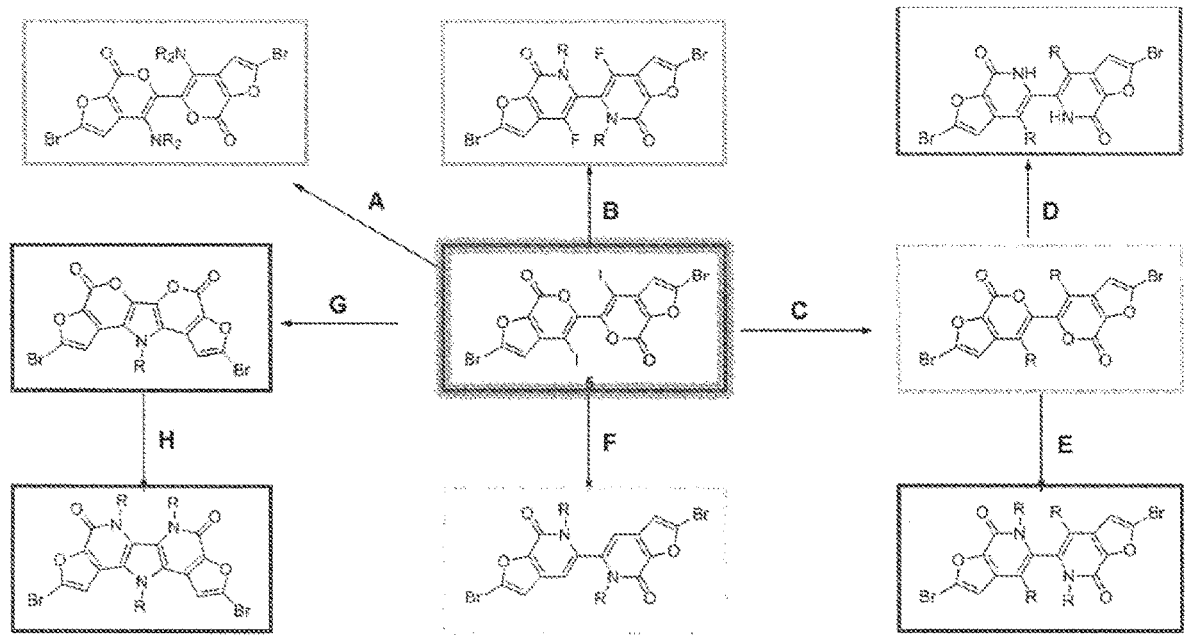
FIG. 3 is a chemical reaction diagram illustrating methods of forming various molecules starting from a dibromo-diiodo-bifuropyranone heterocycle according to at least one embodiment.

As shown in FIG. 3, the DBDFP heterocycle (5) can be used to synthesize disubstituted-amino-bifuropyranones by substitution of secondary amine groups for the iodine atoms under Hartwig-Buchwald cross-coupling conditions as shown in reaction A. Reaction A may be performed in a solvent such as DMF, dioxane, dimethyl ether, chlorobenzene, toluene, or THF and at a temperature ranging from about 55 degrees C. to about 100 degrees C. The reaction uses a palladium catalyst such as [1,1'-Bis(diphenylphosphino)ferrocene]dichloropalladium(II) or Bis(dibenzylideneacetone)palladium(0) and tri(o-tolyl)phosphine, and a base such as sodium tert-butoxide, and a secondary amine reagent HNR$_2$, where R includes the following or combinations of the following: C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, and heterosubstituted linear, branched, cyclic and aromatic groups. Branched alkyl chains may be, or may include, secondary and tertiary carbon atoms. Linear alkyl chains may also be perfluorinated (i.e., replacing each hydrogen on the alkyl chain with a fluorine atom).

The DBDFP heterocycle (5) can be used to synthesize difluoro-N-substituted bifuropyridinones by subsequent metal-catalyzed fluorination and amination reactions as shown in reactions B. The fluorination of the reactions B may be performed in a solvent such as DMF, DMSO, or toluene, using a fluorinating reagent such as silver fluoride or tetramethyl ammonium fluoride, a catalyst such as commercially available (t-BuCN)$_2$CuOTf or Palladium (0) catalysts, a commercially available ligand such as BrettPhos, under an inert atmosphere such as nitrogen or argon, and at a temperature range from 25 to 170 degrees C. The amidation reaction may be performed in the presence of a primary amine, such as H$_2$NR, at elevated temperatures of at least 80 degrees C., and may be performed neat, in the absence of a solvent, or with a suitable solvent.

The DBDFP heterocycle (5) can be used to synthesize disubstituted-bifuropyranones in two steps by subsequent Sonogashira cross-coupling reaction of the DBDFP with an alkyne followed by complete hydrogenation of the alkyne as shown in reaction C. Reaction C may be performed in a solvent such as DMF, THF, dioxane, dichloromethane, chloroform, and ethanol or combination thereof, and at a temperature range from 25 to 130 degrees C. The first step of reaction C may be performed using a commercially available catalyst such as Pd(PPh$_3$)$_2$Cl$_2$, and the hydrogenation step is performed under a hydrogen atmosphere over supported palladium catalyst at a pressure range of 1-500 PSI. Other suitable metal hydrogenation catalysts known in the art may also be used.

The disubstituted-bifuropyranones from reaction C can be used to synthesize disubstituted-bifuropyridinones by amidation using ammonium hydroxide as a reagent, and may be performed at elevated temperatures up to 100 degrees C. as shown in reaction D.

The disubsituted-bifuropyranones from reaction C can also be used to synthesize N-substituted disubstituted-bifuropyridinones by amidation using a primary amine as a reagent, as shown in reaction E, at elevated temperatures of at least 80 degrees C., and may be performed neat, in the absence of a solvent, or with a suitable solvent. The groups attached to the nitrogen atoms in the products of reaction E may be the same as, or different from, the groups attached to the carbon atoms in these products.

The DBDFP heterocycle (5) can be used to synthesize N-substituted bifuropyridinones directly by subsequent dehalogenation and amidation with a primary amine as shown in reaction F. The dehalogenation may be accomplished by using a continuous flow reactor with an iridium catalyst, such as commercially available fac-Ir(ppy) (tris[2-phenylpryidinato-c$^2$,N]iridium(III)), in the stationary phase, and a mobile phase of acetic acid and tributylamine. This dehalogenation process may also be accomplished in a single reaction vessel using reagents paraformaldehyde and cesium carbonate, a catalyst of palladium acetate, in a solution of DMSO at a reaction temperature of 80 degrees C. The amidation reaction may be performed in the presence of a primary amine, such as that used in reaction E, at elevated temperatures of at least 80 degrees C., and may be performed neat, in the absence of a solvent, or with a suitable solvent.

The DBDFP heterocycle (5) can be used to synthesize fused pyrrolo-bifuropyranones by Hartwig-Buchwald cross-coupling with a primary amine as shown in reaction G. Reaction G may be performed in a solvent such as dimethyl formamide, dioxane, dimethyl ether, chlorobenzene, toluene or THF and at a temperature ranging from about 55 degrees C. to about 100 degrees C. The reaction may include a palladium catalyst such as [1,1'-B is(diphenylphosphino) ferrocene]dichloropalladium(II) or Bis(dibenzylideneacetone)palladium(0) and tri(o-tolyl)phosphine, and a base such as sodium tert-butoxide.

The fused pyrrolo-bifuropyranones of reaction G can be used to synthesize N-substituted pyrrolo-bis-N-substituted bifuropyridinones by amidation similar to reaction E, using a parimary amine as shown in reaction H. Reaction H is performed at elevated temperatures of at least 80 degrees C., and may be performed neat, in the absence of a solvent, or with a suitable solvent. The groups attached to the nitrogen atoms of the pyridinone structures may be the same as, or different from, the group attached to the nitrogen atom of the pyrrolo group, as driven by the reagents used to react with compound (5).

The R-groups present on the various acceptor molecules (products of reactions A, B, C, D, E, F, G, H) may include the following or combinations of the following: C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, and heterosubstituted linear, branched, cyclic and aromatic groups. Branched alkyl chains may be, or may include, secondary and tertiary carbon atoms. Linear alkyl chains may also be perfluorinated (i.e., replacing each hydrogen on the alkyl chain with a fluorine atom). It should also be noted that for any Sonogashira reaction, the alkyne is a terminal alkyne.

Each of the acceptor molecules can be polymerized via palladium-catalyzed cross-coupling reactions with donor molecules to form new D-A copolymers.

Figure 4:
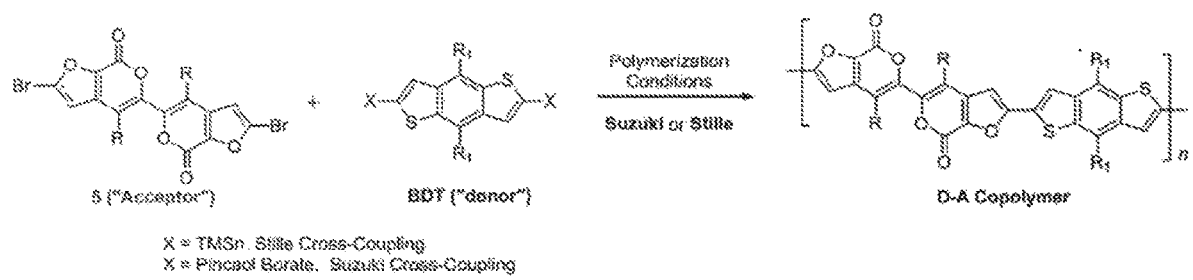
FIG. 4 is a chemical reaction diagram illustrating methods of forming a donor-acceptor copolymer according to at least one embodiment.

FIG. 4 shows an example of a palladium catalyzed cross-coupling polymerization between one of the molecules shown in FIG. 3 (including DBDFP heterocycle (5)), for example a disubstituted-bifuropyranone (product from reactions C), and a representative donor molecule, for example a benzodithiophene (BDT, IUPAC 1,5-dithia-s-indacene with the indicated substitutions at 2, 4, 6, and 8 positions), to form a D-A copolymer. The donor molecule, such as BDT, may be functionalized with either trialkylstannanes for Stille cross-coupling polymerizations, or boronic acids/esters for Suzuki cross-coupling polymerizations.

In one embodiment, Stille cross-coupling is used for the polymerization reaction, where X is trimethylstannane ("TMSn") and R$_1$ includes the following or combinations of the following: C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, and heterosubstituted linear, branched, cyclic and aromatic groups. Branched alkyl chains may be, or may include, secondary and tertiary carbon atoms. Linear alkyl chains may also be perfluorinated (i.e., replacing each hydrogen on the alkyl chain with a fluorine atom). The Stille cross-coupling may be performed at or above a temperature of 120 degrees C., and in a solvent such as toluene, DMF, chlorobenzene, or a combination thereof.

In another embodiment, Suzuki cross-coupling is used for the polymerization reaction, where X is pinacol borate and R$_1$ includes the following or combinations of the following: C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, and heterosubstituted linear, branched, cyclic and aromatic groups. Branched alkyl chains may be, or may include, secondary and tertiary carbon atoms. Linear alkyl chains may also be perfluorinated (i.e., replacing each hydrogen on the alkyl chain with a fluorine atom). The Suzuki cross-coupling may be performed at room temperature (about 20 degrees C.), and in a solvent such as toluene, DMF, chlorobenzene, or a combination thereof.

Figure 5:
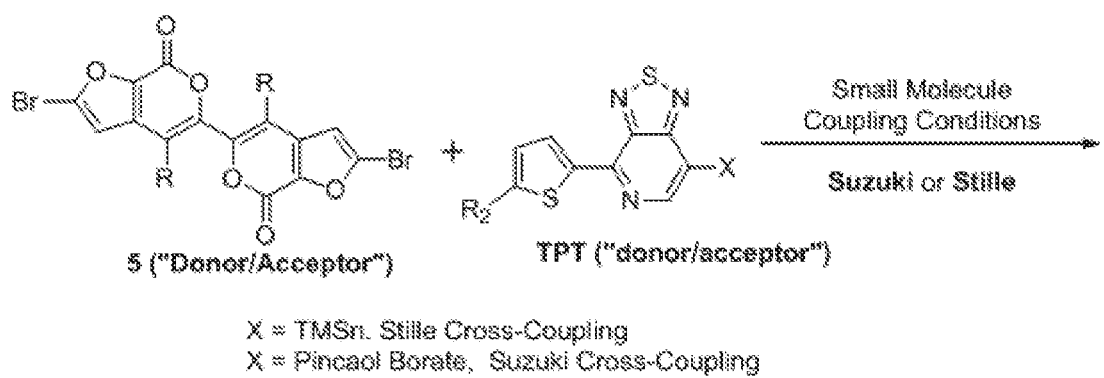
FIG. 5 is a chemical reaction diagram illustrating methods of forming a donor-acceptor small molecule according to at least one embodiment.
Figure 5:
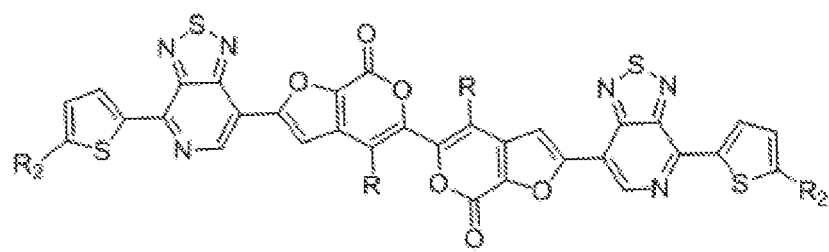

FIG. 5 shows an example of a palladium catalyzed cross-coupling reaction between one of the molecules shown in FIG. 3 (including DBDFP heterocycle (5)), such as a disubstituted-bifuropyranone (product from reactions C), and a representative donor or acceptor molecule from the TPT (thiophene-pyridyl-thiadiazole) class of donor-acceptor molecules, for example a thienyl-thiatriazaindene small molecule donor-acceptor (the "TPT" molecule in FIG. 5 is a 4-(5-$R_2$ylthiophen-2-yl)-[1,2,5]thiadiazolo[3,4-c]pyridine, where "$R_2$yl" is a name of an alkyl chain), to form a D-A small molecule (1). In some embodiments, the TPT molecule may act as an electron acceptor while the disubstituted-bifuropyranone acts as an electron donor. In other embodiments, the TPT molecule may act as an electron donor while the disubstituted-bifuropyranone acts as an electron acceptor.

In one embodiment, Stille cross-coupling is used for the reaction, where X is TMSn and $R_2$ includes the following or combinations of the following: hydrogen, C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, and heterosubstituted linear, branched, cyclic and aromatic groups. Branched alkyl chains may be, or may include, secondary and tertiary carbon atoms. Linear alkyl chains may also be perfluorinated (i.e., replacing each hydrogen on the alkyl chain with a fluorine atom). The Stille cross-coupling may be performed at a temperature above 120 degrees C., and in a solvent such as toluene, DMF, chlorobenzene, or a combination thereof.

In another embodiment, Suzuki cross-coupling is used for the reaction, where X is pinacol borate and $R_2$ includes the following or combinations of the following: hydrogen, C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, and heterosubstituted linear, branched, cyclic and aromatic groups. Branched alkyl chains may be, or may include, secondary and tertiary carbon atoms. Linear alkyl chains may also be perfluorinated (i.e., replacing each hydrogen on the alkyl chain with a fluorine atom). The Suzuki cross-coupling may be performed at the room temperature (about 20 degrees C.), and in a solvent such as toluene, DMF, chlorobenzene, or a combination thereof.

Figure 6:
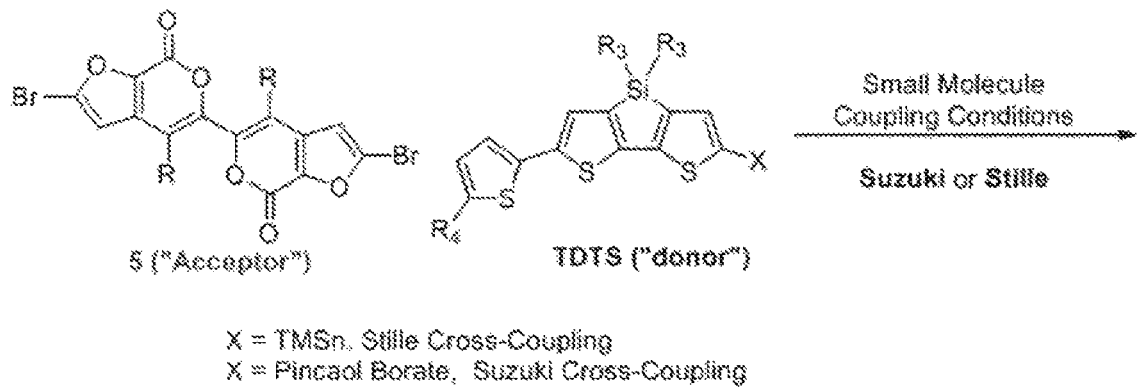
FIG. 6 is a chemical reaction diagram illustrating methods of forming a donor-acceptor small molecule according to at least one embodiment.
Figure 6:
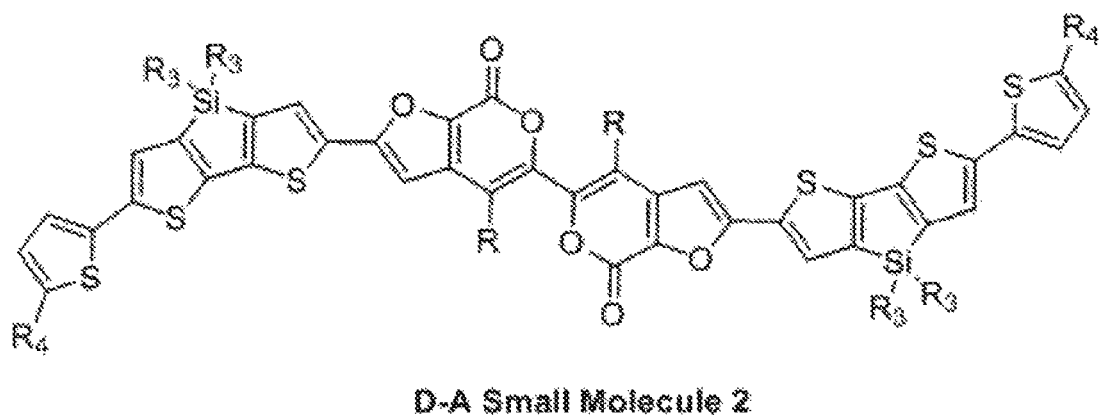

FIG. 6 shows an example of a palladium-catalyzed cross-coupling reaction between one of the molecules shown in FIG. 3 (including DBDFP heterocycle (5)), for example disubstituted-bifuropyranone (product from reactions C), and an electron rich molecule, for example a thienyl dithienosilole (TDTS, in this case a 3-(2H-1$\lambda^{4-5}$-$R_2$-thien-2-yl)-1,1-$R_3$-6-X-4,5-s-dithieno-disilole), to form a D-A small molecule (2). In one embodiment, Stille cross-coupling is used for the reaction, where X is TMSn. In another embodiment, Suzuki cross-coupling is used where X is pinacol borate. The Stille cross-coupling may be performed at a temperature above 120 degrees C., and in a solvent such as toluene, DMF, chlorobenzene, or a combination thereof. The Suzuki cross coupling may be performed at the room temperature (about 20 degrees C.), and in a solvent such as toluene, DMF, chlorobenzene, or a combination thereof.

In FIG. 6, $R_3$ includes the following or combinations of the following: C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, and heterosubstituted linear, branched, cyclic and aromatic groups. Branched alkyl chains may be, or may include, secondary and tertiary carbon atoms. Linear alkyl chains may also be perfluorinated (i.e., replacing each hydrogen on the alkyl chain with a fluorine atom), and $R_4$ includes the following or combinations of the following: hydrogen, C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, and heterosubstituted linear, branched, cyclic and aromatic groups. Branched alkyl chains may be, or may include, secondary and tertiary carbon atoms. Linear alkyl chains may also be perfluorinated (i.e., replacing each hydrogen on the alkyl chain with a fluorine atom).

As shown in FIGS. 4, 5, and 6, the DFP, such as DBDFP derived acceptor molecules (or donor molecules in some embodiments) can be paired with either electron rich molecules or electron deficient molecules to form polymers or small molecules. The band-gap of the small molecules can be tuned by selecting different donors or acceptors. The D-A copolymers or small molecules are blended with an n-type material (i.e., phenyl-C61-butyric acid methyl ester, perylenediimide, etc.), and the blend is used as the active layers of an OPV. In addition, because the DFP, such as DBDFP, derived acceptor molecules (or donor molecules) have either a biisocoumarin or biisoquinoline core structure and can be easily varied to yield a different functional backbone or different substituents, the solubility of the D-A copolymer or small molecules can be adjusted to meet the requirements of various applications.

While the foregoing is directed to embodiments of the present disclosure, other and further embodiments of the present disclosure may be devised without departing from the basic scope thereof.

What is claimed is:

1. A method for forming a polymer or a small molecule to be used in organic photovoltaics, comprising:
    forming a dibromo-diiodo-furopyran having the structure

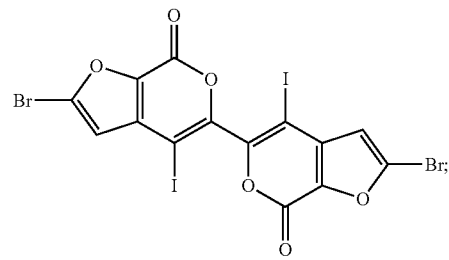 [SMILES: O=c1oc(-c2oc(=O)c3oc(Br)cc3c2I)c(I)c2cc(Br)oc12]

and
    forming a small molecule or a polymer from a reaction mixture comprising the dibromo-diiodo-furopyran.

2. The method of claim 1, wherein the small molecule is formed by substitution of dialkylamines for iodines in the dibromo-diiodo-furopyran under Hartwig-Buchwald cross-coupling conditions, wherein the small molecule is a dialkylamino-bifuropyranone.

3. The method of claim 1, wherein the small molecule is formed by copper-catalyzed fluorination and amination of the dibromo-diiodo-furopyran, wherein the small molecule is a difluoro-N-substituted bifuropyridinone.

4. The method of claim 1, wherein the small molecule is formed by Sonogashira cross-coupling of the dibromo-diiodo-furopyran with an alkyne followed by complete hydrogenation of the alkyne, wherein the small molecule is a disubstituted-bifuropyranone.

5. The method of claim 4, further comprising reacting the disubstituted-bifuropyranone with hydroxylamine to form a disubstituted-bifuropyridinone.

6. The method of claim 4, further comprising reacting the disubstituted-bifuropyranone with a primary amine to form an N-substituted disubstituted-bifuropyridinone.

7. The method of claim 4, further comprising performing a palladium-catalyzed cross-coupling polymerization between the disubstituted-bifuropyranone and an electron donor molecule to form the polymer.

8. The method of claim 7, wherein the electron donor molecule is benzodithiophene.

9. The method of claim 7, wherein the palladium-catalyzed cross-coupling polymerization is a Stille cross-coupling polymerization.

10. The method of claim 7, wherein the palladium-catalyzed cross-coupling polymerization is a Suzuki cross-coupling polymerization.

11. The method of claim 4, further comprising performing a palladium-catalyzed cross-coupling reaction between the disubstituted-bifuropyranone and a compound to form the small molecule, wherein the compound has the structure:

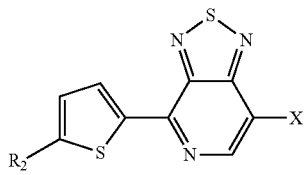

wherein:
X is trimethylstannane or pinacol borate, and
R$_2$ is selected from the group consisting of hydrogen, C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, heterosubstituted C1-C20 linear alkyl chains, heterosubstituted C2-C24 branched alkyl chains, heterosubstituted C1-C24 branched alkyl chains, cyclic groups, heterosubstituted cyclic groups, aromatic groups, heterosubstituted aromatic groups, and a combination thereof.

12. The method of claim 11, wherein the palladium-catalyzed cross-coupling reaction is a Stille cross-coupling reaction.

13. The method of claim 11, wherein the palladium-catalyzed cross-coupling reaction is a Suzuki cross-coupling reaction.

14. The method of claim 4, further comprising performing a palladium-catalyzed cross-coupling reaction between the disubstituted-bifuropyranone and a compound to form the small molecule, wherein the compound has the structure:

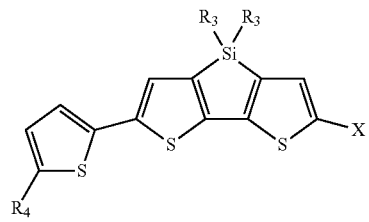

wherein:
X is trimethylstannane or pinacol borate,
R$_3$ is selected from the group consisting of Cl-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, heterosubstituted C1-C20 linear alkyl chains, heterosubstituted C2-C24 branched alkyl chains, heterosubstituted C1-C24 branched alkyl chains, cyclic groups, heterosubstituted cyclic groups, aromatic groups, heterosubstituted aromatic groups, and a combination thereof, and R$_4$ is selected from the group consisting of hydrogen, C1-C20 linear alkyl chains, C2-C24 branched alkyl chains, monoalkyl amines comprised of C2-C20 linear alkyl chains or C1-C24 branched alkyl chains, dialkylamines comprised of C1-C20 linear alkyl chains or C1-C24 branched alkyl chains, heterosubstituted C1-C20 linear alkyl chains, heterosubstituted C2-C24 branched alkyl chains, heterosubstituted C1-C24 branched alkyl chains, cyclic groups, heterosubstituted cyclic groups, aromatic groups, heterosubstituted aromatic groups, and a combination thereof.

* * * * *